(12) United States Patent
Danoff et al.

(10) Patent No.: US 7,431,734 B2
(45) Date of Patent: Oct. 7, 2008

(54) IMPLANTED PROSTHETIC DEVICE

(75) Inventors: Jonathan R. Danoff, Great Neck, NY (US); Jared E. D. Bernheim, Holliswood, NY (US)

(73) Assignee: IntelliStem Orthopaedic Innovations, Inc., Philadelphia, PA (US)

( * ) Notice: Subject to any disclaimer, the term of this patent is extended or adjusted under 35 U.S.C. 154(b) by 208 days.

(21) Appl. No.: 11/347,925

(22) Filed: Feb. 6, 2006

(65) Prior Publication Data

US 2006/0190080 A1    Aug. 24, 2006

Related U.S. Application Data

(60) Provisional application No. 60/649,968, filed on Feb. 4, 2005.

(51) Int. Cl.
*A61F 2/28* (2006.01)
*A61N 1/00* (2006.01)

(52) U.S. Cl. .............. 623/16.11; 623/18.11; 623/20.17; 623/23.16; 607/51

(58) Field of Classification Search .............. 623/23.49, 623/18.12, 16.11–23.63; 600/9–15; 606/60–75; 607/50–52, 117
See application file for complete search history.

(56) References Cited

U.S. PATENT DOCUMENTS

| | | | |
|---|---|---|---|
| 3,820,534 A | 6/1974 | Kraus et al. |
| 4,027,392 A | 6/1977 | Sawyer et al. |
| 4,175,565 A | 11/1979 | Chiarenza et al. |
| 4,195,367 A | 4/1980 | Kraus |
| 4,216,548 A | 8/1980 | Kraus |
| 4,558,701 A | 12/1985 | Spalten |
| 4,665,920 A | 5/1987 | Campbell |
| 4,698,318 A | 10/1987 | Vogel et al. |
| 4,895,574 A | 1/1990 | Rosenberg |
| 5,030,236 A | 7/1991 | Dean |
| 5,032,129 A | 7/1991 | Kurze et al. |
| 5,298,602 A | 3/1994 | Shikinami et al. |
| 5,383,935 A | 1/1995 | Shirkhanzadeh |
| 5,456,724 A | 10/1995 | Yen et al. |
| 5,684,061 A | 11/1997 | Ohnishi et al. |

(Continued)

FOREIGN PATENT DOCUMENTS

JP    07096042    4/1995

(Continued)

OTHER PUBLICATIONS

International Search Report of PCT/US06/04118 filed Feb. 6, 2006.

(Continued)

*Primary Examiner*—Bruce E. Snow
(74) *Attorney, Agent, or Firm*—Leydig, Voit & Mayer, Ltd.

(57) ABSTRACT

An orthopedic device adapted for implantation into a body where it contacts bone tissue is disclosed which has at least one spaced apart polarized magnetic element, at least one piezoelectric element or a combination of a polarized magnetic element and a piezoelectric element which are in direct contact with one another or are separately mounted on the implant. The piezoelectric element being at least partially embedded in a surface of the device which contacts bone tissue for the promotion of osteogenesis or osseointegration.

4 Claims, 5 Drawing Sheets

U.S. PATENT DOCUMENTS

| | | |
|---|---|---|
| 5,733,292 A | 3/1998 | Gustilo et al. |
| 5,759,205 A | 6/1998 | Valentini |
| 5,876,446 A * | 3/1999 | Agrawal et al. .......... 623/23.61 |
| 6,034,295 A | 3/2000 | Rehberg et al. |
| 6,120,502 A | 9/2000 | Michelson |
| 6,143,035 A | 11/2000 | McDowell |
| 6,168,633 B1 | 1/2001 | Shoher et al. |
| 6,241,771 B1 | 6/2001 | Gresser et al. |
| 6,368,325 B1 | 4/2002 | McKinley et al. |
| 6,447,542 B1 | 9/2002 | Weadock |
| 6,481,440 B2 | 11/2002 | Gielen et al. |
| 6,526,984 B1 | 3/2003 | Nilsson et al. |
| 6,571,130 B1 | 5/2003 | Ljungstrom et al. |
| 6,605,089 B1 | 8/2003 | Michelson |
| 2001/0008980 A1 | 7/2001 | Gresser et al. |
| 2003/0040806 A1 | 2/2003 | MacDonald |
| 2004/0122521 A1 * | 6/2004 | Lee et al. ................. 623/20.15 |
| 2004/0199219 A1 | 10/2004 | Dodge et al. |
| 2005/0228503 A1 | 10/2005 | Gundolf |

FOREIGN PATENT DOCUMENTS

| | | |
|---|---|---|
| SU | 1122329 | 11/1984 |
| WO | WO 95/33416 | 12/1995 |

OTHER PUBLICATIONS

Written Opinion of the International Searching Authority for PCT/US06/04118 filed Feb. 6, 2006.

* cited by examiner

IMPLANTED PROSTHETIC DEVICE

This application claims the priority of Ser. No. 60/649,968, filed Feb. 4, 2005.

BACKGROUND OF THE INVENTION

1. Field of the Invention

The present invention is concerned with implantable orthopedic devices that prevent the loss of bone, stimulate the growth of bone tissue, and enhance fracture healing.

2. Description of the Prior Art

Osteoporosis and other degenerative diseases, including bone trauma, often require the surgical insertion of a prosthetic implant to replace the damaged tissue. The implant must be biocompatible and have the same structural integrity as the tissues it replaces. Replacement of the joints in the hip may require the use of artificial components, in the form of a prosthetic implant inserted into the femur and corresponding acetabulum forming the replacement joint. The knee joint is replaced with two corresponding components, inserted into the femur and tibia, forming the knee joint. These prosthetic implants have been made of stainless steel, cobalt-chromium-molybdenum alloys, titanium alloys, ceramics, and other materials. In order for these materials to be effective as a long term replacement of the joint, the prosthetic implant must provide a good substrate into which the surrounding bone can mechanically integrate and achieve long-term stability. Though much research has been devoted to this concept, these materials fail to achieve excellent mechanical integration and the failure rate of these devices remains high.

Many prosthetic implants have been developed to address implant failure by attempting to enhance the mechanical integration between the implant and the bone. Two such methods stabilizing implantable prosthetic devices are the use of polymethyl methacrylate (PMMA) bone cement and the application of a porous coating on the surface of the implant. The PMMA bone cement can cause harmful side effects and can cause osteolysis which leads to implant failure. In addition, the body may, in response to the implant, form a fibrous tissue capsule surrounding the implant, which causes loosening and failure of the prosthetic device. Failure can also occur if the bone cement fractures or weakens. The technique of porously coating the prosthesis with sintered beads was developed for press-fit implants. These implants do not require cement and achieve a scratch fit against the bone. The bone grows in a three-dimensional nature around these beads, which stabilizes the implant. The porous coat can be applied to either the entire surface, or to proximal sections of the implant so as to facilitate mechanical bonding. The porous coat may also vary according to the size of the sintered bead, which is believed to stimulate different amounts of bone bonding to the implant. This method has had short term success in achieving a mechanical interface with the surrounding bone tissue; however, this application fails in the long-term because of stress shielding, an uneven transfer of weight-bearing stresses to the bone. The porous coat also does not induce a uniform attachment of the bone to the implant substrate which often causes failure of the implant. Lastly, the rate at which the surrounding bone tissue grows into the implant remains slow, which calls for extensive recovery time and there is an increased potential to develop complications.

Bone responds to varying applied stresses and will remodel to best suite those stresses, as recognized by Wolff in 1892. A typical implant reduces stress transfer to the bone in proximal areas around femoral hip implants, while increasing stress transfer in distal areas. This leads to hip pain and eventual bone fracture.

Bone has the ability to detect an externally applied load as a mechanical strain and respond to that strain via tissue remodeling. When stress is applied to a bone in a body, certain materials in bone tissue polarize and exhibit piezoelectric properties. A voltage develops along the loading axis, which stimulates osteoblast cells in the bone matrix to form new bone. At the same time, osteoclast cells break down bone which may account for the similarity in the rates of new bone formation and old bone breakdown, which may maintain bone distribution and bone density at a substantially uniform level. When an orthopedic femoral hip implant is placed in the body, the natural loading environment of the body changes as the regions proximal to the implant receive decreased levels of stress as compared to distal regions. The ultimate result of this phenomenon may be the failure of the implanted prosthesis which will necessitate further surgery.

Attempts have been made to chemically bond implants to bone tissue by the use of a coating of hydroxyapatite or other similar calcium containing chemical compounds. The chemical bonding stabilizes the implant by filling in gaps and providing a cementing effect. The use of chemical compounds does address the problem of protecting the implant from stresses which can cause the implant to loosen and fail. Piezoelectric materials have been used in connection with implants to stimulate bone growth. U.S. Pat. No. 6,143,035 utilizes surface applied piezoelectric elements that are attached to a hip implant with the outer surface polarized to have a negative charge. The piezoelectric element is placed on the medial side of the shoulder or neck of the implant where it will undergo compressive strain. Other embodiments used piezoelectric elements that were mounted on a bone in a position remote from the area where bone growth was desired. Electrical conductors were implanted to conduct the remotely generated current to the site where an implant is placed.

U.S. Pat. No. 6,571,130 discloses a biocompatible piezoelectric element for use as an implanted sensor. U.S. Pat. No. 6,447,542 discloses an implantable porous member that has pores which may be filled with a piezoelectric composition which has the ability to stimulate cell growth by generating an electrical field in response to mechanical stress.

The form and function of the musculo-skeletal system is closely related to the forces acting in its components. Fracture treatment by means of intramedullary nails is an accepted and widely used method of treating transverse and short oblique, axially stable fractures of the femoral diaphysis. However, complications may arise during fracture healing and non-unions, delayed unions, and mal-unions have been reported as well. The introduction of the interlocking nail has allowed treatment of comminuted femoral fractures, because limb rotation and length can be maintained but healing is still a problem in many cases. In femoral nailing, two treatment modalities can be discerned: Static locking connects the implants with the main proximal and distal bone fragments, securing their relative position and orientation. Dynamic locking with fewer connecting screws should prevent rotation while allowing dynamic interfragmentary compression. Experimentally, the beneficial effects of electricity in bone healing have been demonstrated in long bone fracture models. In 1957, Fukada and Yasuda (J.Physiol Soc Jpn 12:1158-1162(1957)) showed that a continuous current of 1 µA over 3 weeks produce new bone growth in rabbit femora. Direct current delivered via electrodes in long bones results in osteogenesis around the negative electrode and resorption around the positive electrode. Ultrasound emitting devices and capacitive coupling devices have been shown to reduce the rates of delayed unions and non-union fractures. Therefore, the present invention also includes the use of direct current stimulation of bone growth by imbedding piezoelectric elements into intramedullary rods and interlocking nails.

The prior art does not disclose the concept of providing below the surface mounted, discrete piezoelectric elements that are positioned in an implantable device in such a manner that they are separated from one another and extend slightly from the surface of the implant, are slightly below the surface of the implant or are flush with the surface of the implant. The use of spaced apart individual piezoelectric elements is believed to make possible the provision of more effective electrical fields for the stimulation of bone growth by locating the piezoelectric elements where the bone growth is more important to the long term success of the implant. For example, in the case of a hip implant, bone growth at the upper end of the femur is more important than in other areas contacted with the implant because of the higher stresses that are applied to the upper end of the femur.

SUMMARY OF THE INVENTION

The present invention provides an orthopedic device adapted for implantation into a body where it contacts bone tissue, said device having at least one spaced apart polarized magnetic element, at least one piezoelectric element or a combination of a polarized magnetic element and a piezoelectric element which are in direct contact with one another or are separately mounted on said device, said element being at least partially embedded in a surface of said device which contacts bone tissue, said element being positioned to be in direct electrical contact with bone tissue for the promotion of osteogenesis or osseointegration.

Accordingly, it is a principal object of this invention to provide improved orthopedic implant devices that have embedded in a surface a material that promotes osteogenesis or osseointegration.

It is also an object of the invention to provide improved methods and produce internal fixation devices to promote the healing of fractures.

It is also an object of this invention to reduce the time required for complete healing of bone trauma after the implantation of orthopedic devices.

DETAILED DESCRIPTION OF THE INVENTION

Figure 1:
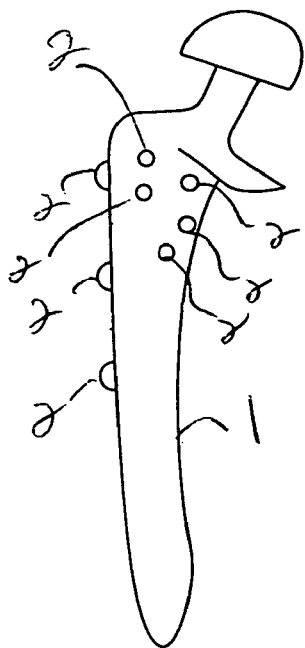
FIG. 1 is a side view of a hip implant which shows a plurality of piezeoelectric ceramic elements embedded in the surface with a portion of the piezoelectric element extending above the surface of the hip implant.

The present invention is an improved implantable orthopedic device that is intended to provide accelerated or enhanced bone formation around the implant as compared to the normal bone growth that occurs in response to the implantation of artificial materials in the body. The particular implants that may be adapted for use in connection with the invention include virtually all implantable devices such as dental implants, hip joints, knee joints, finger joints, bone fixation devices, spinal implants, intramedullary rods, intramedullary nails, and the like, whether for human or veterinary applications.

The piezoelectric element that is used in the invention may be made of any non-toxic, biocompatible material that will generate an amount of electric current that will stimulate bone growth under the normal stress that bone structure receives due to walking, running, standing, chewing and the like. The current that is generated by the piezoelectric element should be between 1 and 250 microamps/cm$^2$, preferably 1-30 microamps/cm$^2$ and should have a voltage of between 0.1 microvolt/cm$^2$ and 10 volts/cm$^2$ of bone tissue but preferably between 1 microvolt/cm$^2$ and 300 microvolts/cm$^2$. The materials that may be used to make the piezoelectric elements are commercially available as are the complete piezoelectric elements. Examples of materials that may be used to make suitable piezoelectric elements include barium titanate, hydroxyapatite, apatite, sodium potassium niobate, quartz, PZT (lead zirconium titanate), electret polymers and the like which are mixed with conventional binders and formed into discrete piezoelectric elements. The preferred shape has a circular profile, such as a cylinder with the positive end substantially flat and the other or outer end having a domed shape which is adapted to slide along a bone surface when it is fitted into a bone shaft. The elements may be from 0.02 mm to 2 mm high with a diameter from 1 mm to 5 mm. Other shapes having flat surfaces and squared edges may be utilized. The piezoelectric elements can be polarized in either shear or normal modes. The circular configuration is preferred because drilled holes may be used to facilitate the embedding of the piezoelectric elements in a surface of an implant in implants having a large surface area. In a knee joint, the piezoelectric element may have a ring shape that is placed around the upper and lower post where it is embedded in the transverse surface that abuts each post. A ring shaped piezoeleetric element is placed circumferentially around a medullary nail implant where it is embedded below the metal surface with the upper end being either co-planar with the implant surface or being extended above the surface of the implant. In a bone screw, a ring is placed around the shaft of the screw which abuts the screw head where it is embedded in the transverse surface of the screw head and may also be incorporated into the threaded region of the shaft of the screw body.

Figure 3:
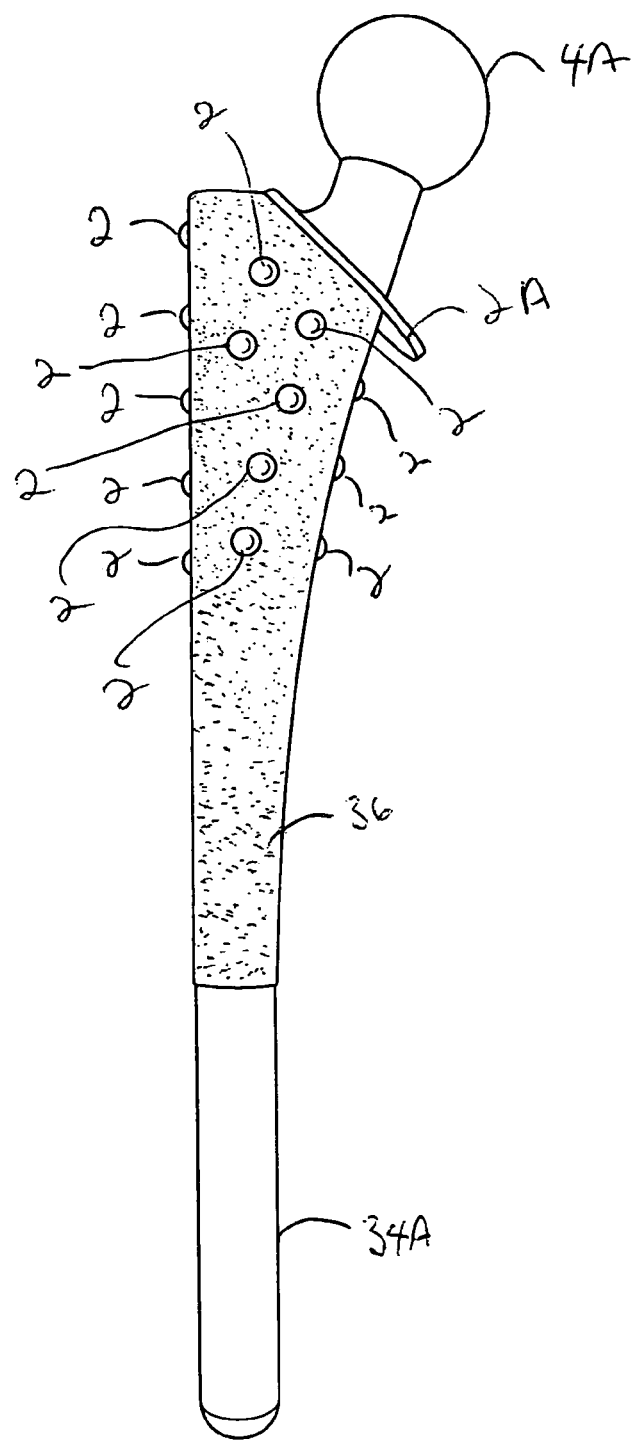
FIG. 3 is a side view of a hip implant where a plurality of spaced apart piezoelectric elements are mounted at the upper portion of the implant and a coating of a bone growth stimulant is placed completely around a major portion of the upper surface of the hip implant.

Generally more than one piezoelectric element will be positioned in an implant to obtain maximum bone growth stimulation without causing any adverse effects. In a hip joint implant, for example, 10-20 individual piezoelectric elements may be embedded in the surface at the upper quarter of the shaft of the hip implant as shown in FIG. 3 because these are the areas which receive the lowest compressive forces. The piezoelectric elements may be placed at any location on the implant where bone growth stimulation is desired. These forces are responsible for the generation of the piezoelectric currents.

Generally in implants where a plurality of piezoelectric elements is utilized, the piezoelectric elements will be spaced apart from one another so that they are spaced from 5 to 500 mm, or more preferably from 5-25 mm apart, depending on the particular implant. It is to be understood that in the case of a knee implant the embedded piezoelectric element may be a single ring like structure which is sized to fit around the individual posts and to fit into a recess around the bottom of the post. The implant maybe affixed to an implant by forming a hole such as a dimple. A dimple is defined to be an indent or a pore which extends below the surface to create a void in any part of the implant that will contact bone tissue. The piezoelectric element may be fixed in the dimple by press fitting a sized piezoelectric element, by an adhesive or by use of machine cut threads, or by forming the piezoelectric element in situ during manufacturing. The negative or the positive pole of the piezoelectric element will be oriented to the outer surface of the implant. The piezoelectric element maybe electrically insulated from the sides of the dimple to enhance the current flow from the implant to the bone tissue. This electric insulation may be any biocompatible dielectric material such as biocompatible glasses or polymers such as ultrahigh molecular weight polyethylene or titanium oxide.

In conjunction with the piezoelectric elements on the surface of an implant, it may be desired to utilize a coating such as hydroxyapatite or other bone growth stimulants or drugs such as resorbable scaffold polymers such as PLA (polylactic acid) or PLLA (poly-L-lactide) or PGA (polyglycolic acid) or antibiotics. As best seen in FIG. 1, the piezoelectric elements 2 are placed on the upper shaft of a conventional hip implant base member 1 in a random spaced apart pattern which is grouped around the upper area of the shaft of the implant where the lowest compressive forces will be expected. If desired, the pattern may be according to an predetermined arrangement such as equal spacing, using the distances disclosed above, around the area where the lowest compressive forces on the implant will be imparted. An enlarged piezoelectric element is shown in the partial cutaway view in FIG. 1A.

Figure 1A:
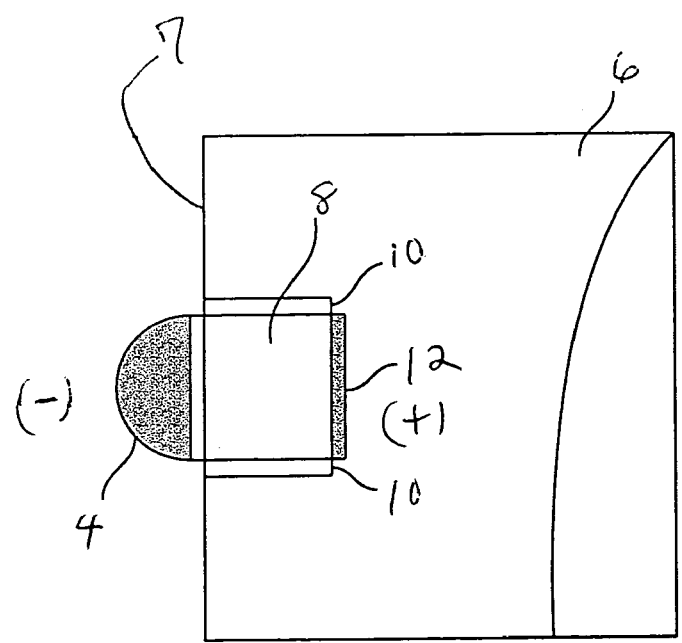
FIG. 1A is an enlarged partially cutaway view of a piezoelectric element that is embedded below the surface of the implant of FIG. 1.
Figure 1B:
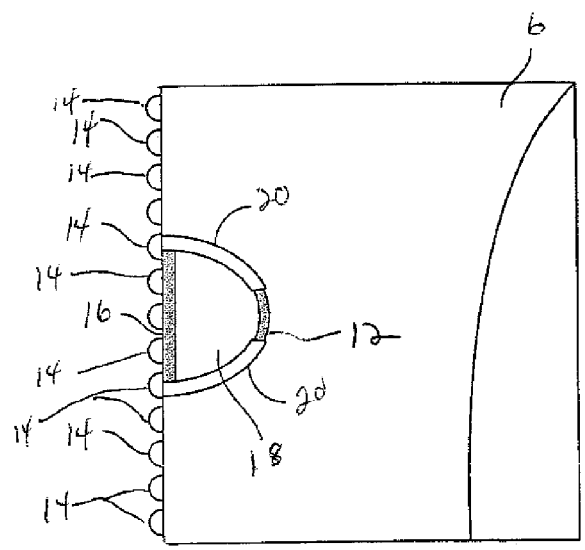
FIG. 1B is an enlarged partially cutaway view of a piezoelectric element cross-section of a piezoelectric element which is mounted flush with the surface of an implant.

As shown in FIG. 1A, a preferred piezoelectric element has a rounded head 4 which extends outward from the implant surface 7 of the implant 6 and a lower part 8 which is embedded below the implant surface 7. The piezoelectric element is provided with an insulator 10 which may be made of ultra high weight polyethylene or titanium oxide or any other suitable non-conductive non-toxic biocompatible material. The insulator is provided around the sides of the piezoelectric element but not at the bottom where a conductive material 12 is placed. The conductive material may be a commercially available biocompatible epoxy composition or it may be a thin layer of a precious metal such as gold or silver. The (−) and (+) symbols indicate the orientation of the respective negative and positive poles of the piezoelectric element. This is because the preferred piezoelectric element is polarized for maximum efficiency in producing electric current. The piezoelectric element may be made of barium titanate and a convention binder or composite of barium titanate hydroxyapatite. These piezoelectric elements are commercially available and preferred sizes may have a diameter of from 1 to 5 mm and a height of from 0.02 mm to 2 mm. The height to which the dome shaped end of the piezoelectric element extends from the surface of the implant should not exceed the height of the typical roughened surface of an implant which may be between 0.02 mm to 2 mm. FIG. 1B illustrates an additional embodiment where a piezoelectric element 18 has a substantially flat outer surface 16 which is mounted flush with the surface of an implant 6. The surface of this embodiment is also provided with conventional beads 14 which cover the surface. This type of a surface is conventionally utilized for the surface of an implant in order to provide sites that will press on bone tissue for the purpose of stimulating bone growth and implant stabilization. An insulator 20 is provided on both sides of the piezoelectric element 18 and a conductor 12, such as the conductor 12 of FIG. 1A is also provided at the bottom.

Figure 2:
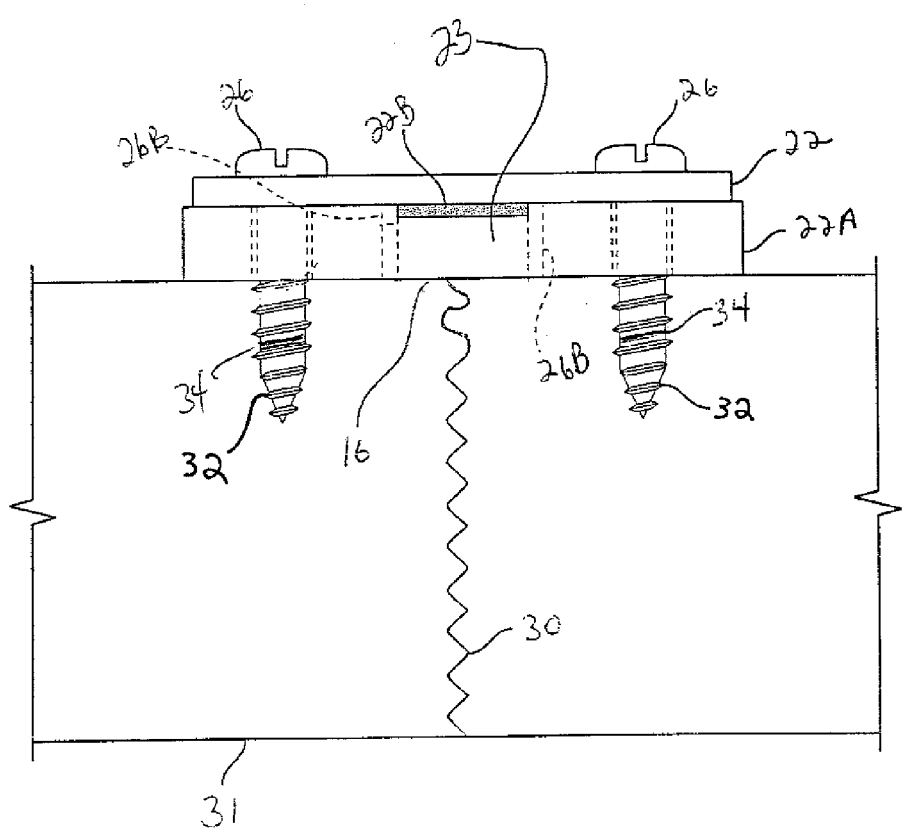
FIG. 2 is a side view of a conventional bone plate that is used to fasten two broken bones together where the bone plate has been modified by embedding a piezoelectric element within the surface of the bone plate with a part of the piezoelectric element extending above the surface.

FIG. 2 is a partial cutaway side-view of a bone plate 22A which is provided with an auxiliary backing bone plate 22. The plate 22A is affixed across a broken bone 31 at break 30 with screws 26. The auxiliary bone plate 22 is an optional component that is used to provide a means of having the tightened screws 26 apply additional compressive force to the bone plate 22A and ultimately to the bone 31. The bone plate is held in position across the fracture line 30 and screws 26 have threads 32 which may optionally be provided with an additional coating of a bone growth stimulating material such as polarized hydroxyapatite at screw shaft areas 34. The piezoelectric element 23 is fitted into bone plate 22A with insulation 26B placed around the sides and a conductor 22B at the bottom with the top 16 flush mounted.

Figure 4:
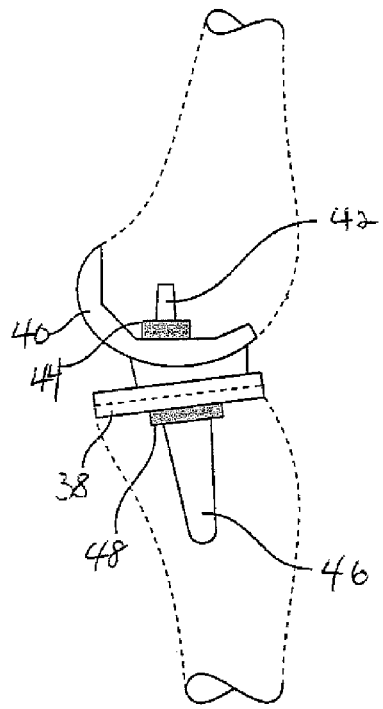
FIG. 4 is a phantom side view of an implanted knee joint where the mounting posts have been modified by adding a piezoelectric element which is partially embedded at the mounting post of both the upper and lower posts of the knee joint.

FIG. 3 is a side view of a femur implant which has embedded piezoelectric elements 2 at the upper end and also has a coating 36 of a bone growth stimulant. The lower shaft 34A is shown without any growth stimulant coating but such a coating may be applied if desired. Proximal collar 2A is an optional feature of the hip implant which may be omitted if desired. The ball 4A is also optional as the implant may be supplied without the ball 4A. FIG. 4 is a cutaway view of a conventional implanted knee joint having a lower tibial part 38 and an upper femur part 40. Upper femur part 40 has a centrally located post 42 which is adapted to be implanted into an enlarged medullary space in the femur. At the lower portion of the post 42, a thin, circular piezoelectric ring 44 is fitted around the post so that it contacts a portion of the femur when the implant is in place. The lower tibial part 38 also has a post 46 which is adapted for insertion into an enlarged medullary space in the tibia. A second thin, circular piezoelectric ring 48 is provided around centrally located post 46. Generally the thin, circular piezoelectric ring which have a thickness of 1 to 5 mm and a hole that is sized to engage a post in an implantable knee joint. The total diameter will range from about 1 to 5 mm.

Figure 5:
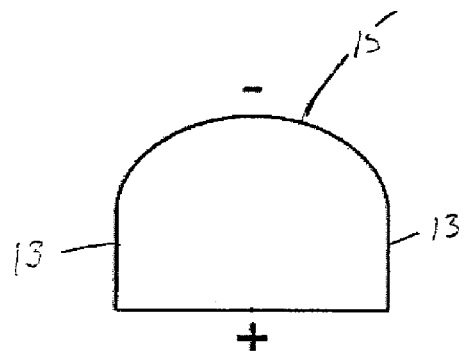
FIG. 5 is a side view of a domed top, cylindrical shaped piezoelectric element adapted for use in the invention.

FIG. 5 is a side perspective of a piezoelectric element adapted to be fitted in a drilled hole in a surface of an implantable orthopedic device. The piezoelectric device is generally cylindrical in shape with a domed top 15 and straight sides 13.

Figure 6:
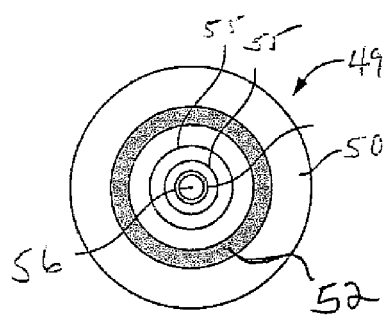
FIG. 6A is a bottom view of a bone screw having a piezoelectric ring placed under the head of the screw.
FIG. 6B is a side view of the bone screw of FIG. 6A having a ring abutting the head and piezoelectric elements fitted into the screw threads.
Figure 6:
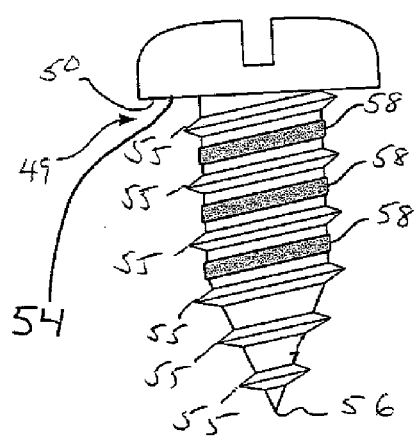

FIG. 6A is a bottom view of an orthopedic screw 49 that may be utilized to fix various types of fractures. The head 50 is provided with a recessed piezoelectric ring 52 that is flush mounted with the bottom surface 54 of screw of the head as shown in FIG. 6B. The tip of the screw 56 is pointed to facilitate insertion into a bone and optional lateral piezoelectric elements 58 may be placed on the shaft of the screw to stimulate bone growth. Conventional threads 55 hold the screw in the bone.

Figure 7:
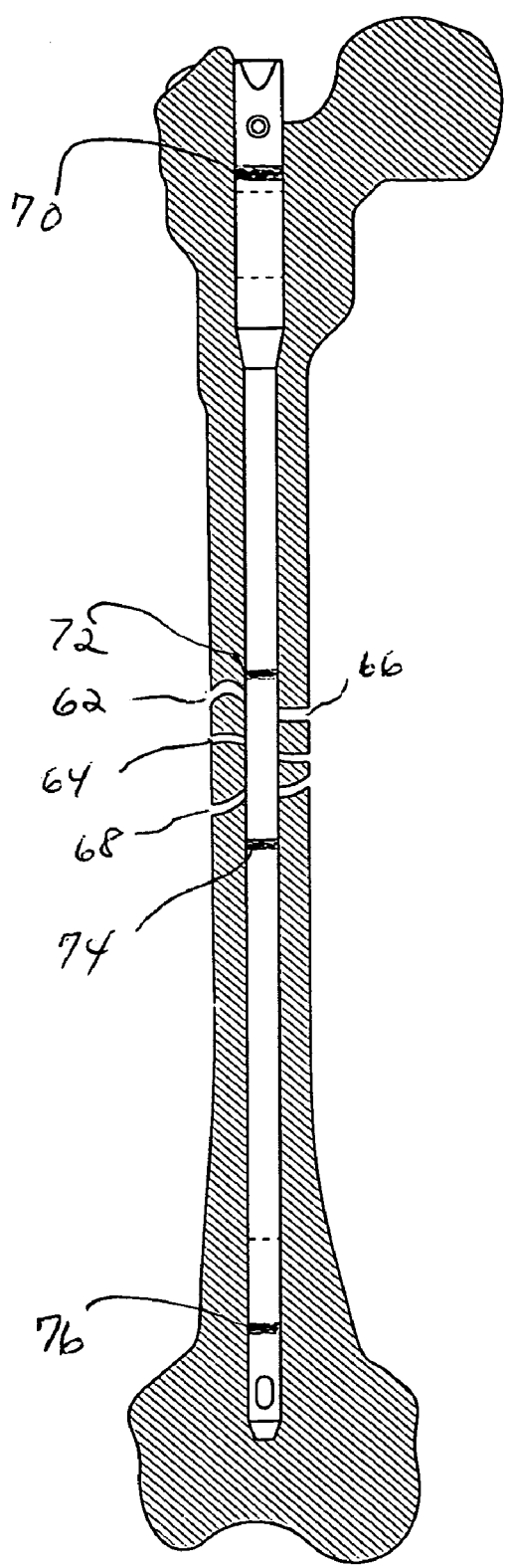
FIG. 7 is a cross sectional view of an intramedullary rod implant in a tibia where piezoelectric rings are affixed to the intramedullary rod above and below the fracture and at the end.

FIG. 7 is a cross section of a fractured femur in which a intramedullary rod has been placed in order to stabilize the fractures 62, 64, 66 and 68. Piezoelectric elements 70, 72 and 74 are disposed in a recess which is cut around the shaft of the intramedullary rod so that the piezoelectric elements are flush with the surface of the intramedullary rod and do not interfere with the medulla of the bone shaft during insertion of the rod. The distal end 76 may optionally be provided with an additional piezoelectric ring to promote bone growth at that location.

The invention claimed is:

1. An orthopedic device adapted for implantation into a body and contacting bone tissue, the device comprising:

a surface;

a plurality of spaced apart piezoelectric elements, each piezoelectric element having a top, bottom, and side, the piezoelectric elements being at least partially embedded in the surface, the piezoelectric elements also extending above the surface and being positioned to be in direct electrical contact with bone tissue for the stimulation of bone growth;

a plurality of insulators, each insulator insulating the side of an individual piezoelectric element, but not the top or bottom of the piezoelectric element;

a plurality of conductive elements, each conductive element located at the bottom of an individual piezoelectric clement.

2. The device of claim 1, further comprising a coating on the surface, the coating comprising hydroxyapatite.

3. The device of claim 2, further comprising beads on the surface.

4. The device of claim 1, further comprising beads on the surface.

* * * * *